United States Patent
Kang et al.

(10) Patent No.: US 10,660,532 B2
(45) Date of Patent: May 26, 2020

(54) BLOOD PRESSURE MEASUREMENT APPARATUS, PORTABLE PRESSURE MEASUREMENT APPARATUS, AND CALIBRATION METHOD FOR BLOOD PRESSURE MEASUREMENT APPARATUS

(71) Applicant: SAMSUNG ELECTRONICS CO., LTD., Suwon-si (KR)

(72) Inventors: Jae Min Kang, Seoul (KR); Yong Joo Kwon, Yongin-si (KR); Seung Woo Noh, Seongnam-si (KR); Sang Yun Park, Hwaseong-si (KR); Youn Ho Kim, Hwaseong-si (KR); Young Zoon Yoon, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 362 days.

(21) Appl. No.: 15/493,314

(22) Filed: Apr. 21, 2017

(65) Prior Publication Data
US 2018/0110427 A1 Apr. 26, 2018

(30) Foreign Application Priority Data
Oct. 25, 2016 (KR) .................. 10-2016-0139408

(51) Int. Cl.
*A61B 5/021* (2006.01)
*A61B 5/022* (2006.01)
(Continued)

(52) U.S. Cl.
CPC ........ *A61B 5/02225* (2013.01); *A61B 5/0004* (2013.01); *A61B 5/0261* (2013.01);
(Continued)

(58) Field of Classification Search
CPC . A61B 5/6843; A61B 5/02225; A61B 5/0261; A61B 5/0004; A61B 5/0015;
(Continued)

(56) References Cited

U.S. PATENT DOCUMENTS 5,494,043 A * 2/1996 O'Sullivan ........ A61B 5/02208
600/500
6,533,729 B1 * 3/2003 Khair ..................... A61B 5/021
600/480
(Continued)

FOREIGN PATENT DOCUMENTS

CN 102018500 A 4/2011
KR 10-2008-0083505 A 9/2008
(Continued)

OTHER PUBLICATIONS

Meir Nitzan et al; "Automatic noninvasive measurement of systolic blood pressure using photolethysmography"; BioMedical Engineering OnLine; (http://www.biomedical-engineering-online.com/content/8/1/28); Oct. 26, 2009; pp. 1-8.

*Primary Examiner* — Patricia J Park
*Assistant Examiner* — Victoria Fang
(74) *Attorney, Agent, or Firm* — Sughrue Mion, PLLC

(57) ABSTRACT

A blood pressure measurement apparatus, a portable pressure measurement apparatus, and a calibration method for the blood pressure measurement apparatus are provided. The blood pressure measurement apparatus includes a pulse wave measurer configured to measure pulse wave data of a subject while a user pressurizes and depressurizes the blood pressure measurement apparatus, using a portable pressure measurement apparatus, and a communicator configured to receive pressure data that is applied to the blood pressure measurement apparatus during the pressurizing and the depressurizing of the blood pressure measurement apparatus, from the portable pressure measurement apparatus, the
(Continued)

NON-PRESSURIZE → PRESSURIZE pressure data being measured by the portable pressure measurement apparatus. The blood pressure measurement apparatus further includes a processor configured to update a blood pressure estimation formula, based on the received pressure data and the measured pulse wave data.

10 Claims, 14 Drawing Sheets

(51) Int. Cl.
*A61B 5/1455* (2006.01)
*A61B 5/026* (2006.01)
*A61B 5/00* (2006.01)
*A61B 5/024* (2006.01)

(52) U.S. Cl.
CPC .......... *A61B 5/02108* (2013.01); *A61B 5/681* (2013.01); *A61B 5/7278* (2013.01); *A61B 5/02416* (2013.01); *A61B 2560/0223* (2013.01)

(58) Field of Classification Search
CPC ... A61B 5/0022; A61B 5/021; A61B 5/02108; A61B 5/02116; A61B 5/02125; A61B 5/02141; A61B 5/022; A61B 5/02233; A61B 5/02241; A61B 5/681; A61B 5/6824; A61B 5/7278; A61B 5/02416; A61B 2560/0223; A61B 2562/0247; A61B 2562/0252

USPC .......................................................... 600/479
See application file for complete search history.

(56) References Cited

U.S. PATENT DOCUMENTS

| | | | |
|---|---|---|---|
| 8,086,301 B2 | 12/2011 | Cho et al. | |
| 8,527,038 B2 | 9/2013 | Moon et al. | |
| 9,943,263 B2* | 4/2018 | Lee ........................ | A61B 5/681 |
| 2002/0095092 A1* | 7/2002 | Kondo ............... | A61B 5/02116 |
| | | | 600/503 |
| 2003/0158487 A1* | 8/2003 | Thede .................... | A61B 5/021 |
| | | | 600/485 |
| 2004/0010199 A1* | 1/2004 | Hashimoto .............. | A61B 5/02 |
| | | | 600/502 |
| 2011/0066044 A1 | 3/2011 | Moon et al. | |
| 2011/0306889 A1* | 12/2011 | Di ...................... | A61B 5/02444 |
| | | | 600/499 |
| 2014/0148715 A1 | 5/2014 | Alexander et al. | |
| 2016/0051192 A1 | 2/2016 | Kang et al. | |

FOREIGN PATENT DOCUMENTS

| | | |
|---|---|---|
| KR | 10-2014-0096762 A | 8/2014 |
| KR | 10-2014-0125193 A | 10/2014 |
| KR | 10-1456591 B1 | 10/2014 |
| KR | 10-2016-0049738 A | 5/2016 |

\* cited by examiner

NON-PRESSURIZE        PRESSURIZE

BLOOD PRESSURE MEASUREMENT APPARATUS, PORTABLE PRESSURE MEASUREMENT APPARATUS, AND CALIBRATION METHOD FOR BLOOD PRESSURE MEASUREMENT APPARATUS

CROSS-REFERENCE TO RELATED APPLICATION

This application claims priority from Korean Patent Application No. 10-2016-0139408, filed on Oct. 25, 2016, in the Korean Intellectual Property Office, the disclosure of which is incorporated herein by reference in its entirety.

BACKGROUND

1. Field

Apparatuses and methods consistent with example embodiments relate to a technology for blood pressure measurement, and particularly, to a blood pressure measurement apparatus, a portable pressure measurement apparatus, and a calibration method for the blood pressure measurement apparatus.

2. Description of Related Art

Recently, with an increasing interest in health, various types of biometric information detecting devices have been developed. As various wearable devices that can be worn by a subject have been widely disseminated, devices specialized in health care have been developed.

A cuffless blood pressure sensor is an indirect measurement type blood pressure sensor, which measures a blood pressure by analyzing a pulse wave signal based on an optical signal, rather than a pressure signal of a blood pressure itself. Such a cuffless blood pressure sensor may be calibrated periodically.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, there is provided a blood pressure measurement apparatus including a pulse wave measurer configured to measure pulse wave data of a subject while a user pressurizes and depressurizes the blood pressure measurement apparatus, using a portable pressure measurement apparatus, and a communicator configured to receive pressure data that is applied to the blood pressure measurement apparatus during the pressurizing and the depressurizing of the blood pressure measurement apparatus, from the portable pressure measurement apparatus, the pressure data being measured by the portable pressure measurement apparatus. The blood pressure measurement apparatus further includes a processor configured to update a blood pressure estimation formula, based on the received pressure data and the measured pulse wave data.

The pulse wave measurer may be further configured to emit light to the subject, detect light that is reflected from or absorbed by the subject to which the light is emitted, and acquire the pulse wave data of the subject, based on the detected light.

The processor may be further configured to estimate a reference blood pressure value by performing an oscillometric method, based on the received pressure data and the measured pulse wave data, and update the blood pressure estimation formula, based on the estimated reference blood pressure value.

The processor may be further configured to provide calibration guide information of a method of calibration, using the portable pressure measurement apparatus.

The calibration guide information may include information of a method of the pressurizing and the depressurizing of the blood pressure measurement apparatus, using the portable pressure measurement apparatus.

The blood pressure measurement apparatus may be a wrist wearable device.

According to an aspect of an example embodiment, there is provided a portable pressure measurement apparatus including a pressure sensor configured to measure pressure data that is applied to a blood pressure measurement apparatus while a user pressurizes and depressurizes the blood pressure measurement apparatus, using the portable pressure measurement apparatus, and a communicator configured to transmit the measured pressure data to the blood pressure measurement apparatus. The portable pressure measurement apparatus further includes a pressure buffer configured to be used to maintain a linear pressure change during the pressurizing and the depressurizing of the blood pressure measurement apparatus.

The pressure buffer may be disposed on a surface that is in contact with the blood pressure measurement apparatus during the pressurizing of the blood pressure measurement apparatus, using the portable pressure measurement apparatus.

The pressure buffer may include any one or any combination of latex, polymer, and sponge.

According to an aspect of an example embodiment, there is provided a calibration method for a blood pressure measurement apparatus, the calibration method including measuring pulse wave data of a subject while a user pressurizes and depressurizes the blood pressure measurement apparatus, using a portable pressure measurement apparatus, and receiving pressure data that is applied to the blood pressure measurement apparatus during the pressurizing and the depressurizing of the blood pressure measurement apparatus, from the portable pressure measurement apparatus, the pressure data being measured by the portable pressure measurement apparatus. The calibration method further includes updating a blood pressure estimation formula, based on the received pressure data and the measured pulse wave data.

The updating of the blood pressure estimation formula may further include estimating a reference blood pressure value by performing an oscillometric method, based on the received pressure data and the measured pulse wave data, and updating the blood pressure estimation formula, based on the estimated reference blood pressure value.

The calibration method may further include providing calibration guide information of a method of calibration, using the portable pressure measurement apparatus.

The calibration guide information may include information of a method of the pressurizing and the depressurizing of the blood pressure measurement apparatus, using the portable pressure measurement apparatus.

According to an aspect of an example embodiment, there is provided a blood pressure measurement apparatus including a pulse wave measurer configured to measure pulse wave data of a subject while a user pressurizes and depressurizes a force touch panel, and a pressure measurer including the force touch panel, and configured to measure pressure data that is applied to the blood pressure measurement apparatus during the pressurizing and the depressurizing of the force touch panel. The blood pressure measurement apparatus further includes a processor configured to update a blood pressure estimation formula, based on the measured pressure data and the measured pulse wave data.

The pressure measurer may be further configured to sense a touch area of the force touch panel that the user touches, and a force that the user applies on the force touch panel, and determine the pressure data that is applied to the blood pressure measurement apparatus, based on the sensed touch area and the sensed force.

The processor may be further configured to estimate a reference blood pressure value by performing an oscillometric method, based on the measured pressure data and the measured pulse wave data, and update the blood pressure estimation formula, based on the estimated reference blood pressure value.

The processor may be further configured to provide calibration guide information of a method of calibration, using the force touch panel.

The calibration guide information may include information of a method of the pressurizing and the depressurizing of the force touch panel.

The blood pressure measurement apparatus may be a wrist wearable device.

BRIEF DESCRIPTION OF THE DRAWINGS

The above and/or other aspects will be more apparent by describing example embodiments with reference to the accompanying drawings.

Figure 1:
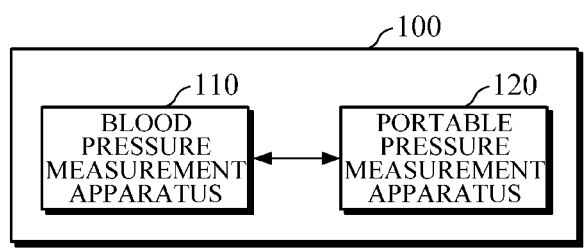
FIG. 1 is a block diagram illustrating a cuffless blood pressure measurement system according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

It may be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described below are selected by considering functions in example embodiments, and meanings may vary depending on, for example, a user or operator's intentions or customs. Therefore, in the following example embodiments, when terms are defined, the meanings of terms may be interpreted based on definitions, and otherwise, may be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements.

Each element may be realized in the form of a hardware component, a software component, and/or a combination thereof.

FIG. 1 is a block diagram illustrating a cuffless blood pressure measurement system 100 according to an example embodiment.

Referring to FIG. 1, the cuffless blood pressure measurement system 100 includes a blood pressure measurement apparatus 110 and a portable pressure measurement apparatus 120.

The blood pressure measurement apparatus 110 may be a cuffless-type blood pressure measurement device capable of non-invasively measuring a blood pressure of a subject. The blood pressure measurement apparatus 110 may be implemented in the form of a software module or fabricated in the form of hardware chip and mounted in an electronic device. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, etc., and the wearable device may include a wristwatch type, a wrist band type, a ring type, a belt type, a necklace type, an ankle band type, a thigh band type, a forearm band type and the like. However, the electronic device is not limited to the above-described examples, and the wearable device is also not limited to the above-described example.

The blood pressure measurement apparatus 110 may operate in blood pressure measurement mode and in calibration mode. The blood pressure measurement mode is a mode for measuring a blood pressure of the subject according to a user's command, and the calibration mode is a mode for updating a blood pressure estimation formula used for blood pressure estimation according to a user's command or a set calibration interval.

In blood pressure measurement mode, the blood pressure measurement apparatus 110 may emit light to the subject, acquire pulse wave data by sensing light reflected from or absorbed by the subject, and estimate a blood pressure by analyzing the acquired pulse wave data.

In calibration mode, the blood pressure measurement apparatus 110 may be calibrated using the portable pressure measurement apparatus 120. For example, when the user pressurizes and depressurizes the blood pressure measurement apparatus 110 using the portable pressure measurement apparatus 120, the blood pressure measurement apparatus 110 may determine a reference blood pressure value (e.g., mean arterial pressure (MAP), systolic blood pressure (SBP), diastolic blood pressure (DBP), etc.) on the basis of pressure data measured by the portable pressure measurement apparatus 120 and pulse wave data measured by the blood pressure measurement apparatus 110 during the process of pressurizing and depressurizing, and be calibrated by updating the blood pressure estimation formula used for blood pressure estimation using the determined reference blood pressure value.

The portable pressure measurement apparatus 120 is used in calibration of the blood pressure measurement apparatus 110. When the user pressurizes and depressurizes the blood pressure measurement apparatus 110 using the portable pressure measurement apparatus 120, the portable pressure measurement apparatus 120 may measure pressure data applied to the blood pressure measurement apparatus 110 during the process of pressurizing and depressurizing, and transmit the measured pressure data to the blood pressure measurement apparatus 110.

Figure 2:
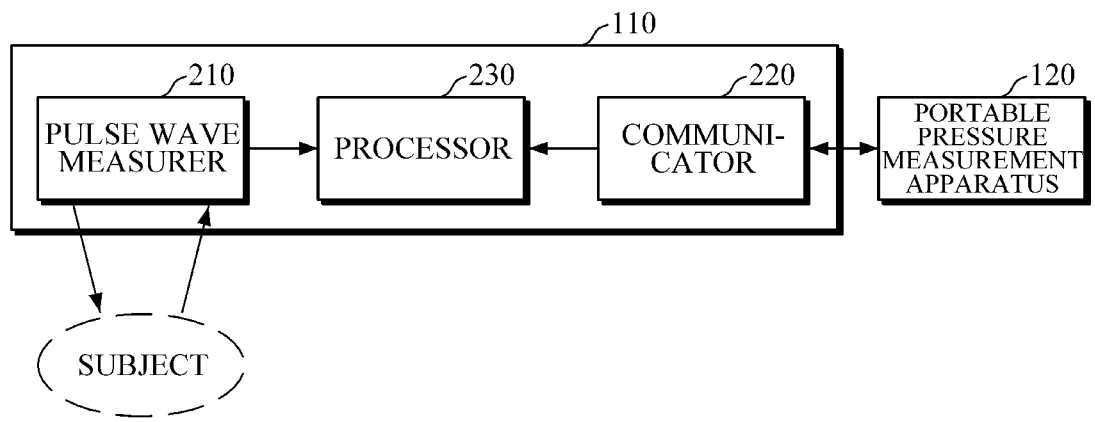
FIG. 2 is a block diagram illustrating a blood pressure measurement apparatus according to an example embodiment.

FIG. 2 is a block diagram illustrating of a blood pressure measurement apparatus 110 according to an example embodiment.

Referring to FIG. 2, the blood pressure measurement apparatus 110 includes a pulse wave measurer 210, a communicator 220, and a processor 230.

The pulse wave measurer 210 may measure pulse wave data of a subject. For example, the pulse wave measurer 210 may emit light to the subject, detect light reflected from or absorbed by the subject, and acquire the pulse wave data of the subject from a detected optical signal.

According to an example embodiment the pulse wave measurer 210 may include a light emitting device and a light receiving device. The light emitting device may include a light emitting diode (LED), a laser diode, and the like, and the light receiving device may include a photodiode, a photo transistor, a charge-coupled device (CCD), and the like.

The communicator 220 may receive, from a portable pressure measurement apparatus 120, pressure data that the user applies to the blood pressure measurement apparatus 110 using the portable pressure measurement apparatus 120. The communicator 220 may use various communication technologies, such as a Bluetooth communication, Bluetooth low energy (BLE) communication, a near-field communication (NFC), a wireless local area network (WLAN) communication, a ZigBee communication, an infrared data association (IrDA) communication, a Wi-Fi direct (WFD) communication, a ultra-wideband (UWB) communication, an Ant+ communication, a Wi-Fi communication, a radio frequency identification (RFID) communication, a 3G communication, a 4G communication, a 5G communication, and the like. However, these are examples, and the communication technologies are not limited to the above examples.

The processor 230 may operate in blood pressure measurement mode or in calibration mode according to a user's command or a set calibration interval.

Hereinafter, operations of the processor 230 in blood pressure measurement mode and in calibration model will be described in detail.

<Blood Pressure Measurement Mode>

The processor 230 may operate in blood pressure measurement mode according to the user's command.

The processor 230 may estimate a blood pressure of the subject by analyzing the pulse wave data measured by the pulse wave measurer 210.

According to an example embodiment, the processor 230 may estimate the blood pressure using a pulse arrival time (PAT) method in which a blood pressure is estimated on the basis of a pulse wave signal and an electrocardiogram (ECG) signal. For example, the processor 230 may extract a feature point of the measured pulse wave (hereinafter, will be referred to as a "pulse wave feature point") and a feature point of an ECG (hereinafter, will be referred to as an "ECG feature point") at the time of measuring the pulse wave, then calculate a time difference between the pulse wave feature point and the ECG feature point (hereinafter, will be referred to as a "pulse wave arrival time"), and finally estimate the blood pressure on the basis of the calculated pulse wave arrival time and the blood pressure estimation formula. In this case, the blood pressure estimation formula may define the relationship between the pulse wave arrival time and the blood pressure. In this example, the processor 230 may calculate the pulse wave arrival time on the basis of the measured pulse wave data, and update the blood pressure estimation formula on the basis of the estimated reference blood pressure value and the calculated pulse wave arrival time.

According to another example embodiment, the processor 230 may estimate a blood pressure using a pulse transit time (PTT) method in which a blood pressure is measured on the basis of a PTT. For example, the processor 230 may extract feature points of pulse waves measured at different two sites, calculate a time difference between the extracted feature points (hereinafter, will be referred to as a "PTT"), and estimate the blood pressure on the basis of the calculated PTT and the blood pressure estimation formula. In this case, the blood pressure estimation formula may define the relationship between the PTT and the blood pressure. In this example, the processor 230 may calculate the pulse transit time on the basis of the measured pulse wave data, and update the blood pressure estimation formula on the basis of the estimated reference blood pressure value and the calculated pulse transit time.

According to still another example embodiment, the processor 230 may estimate a blood pressure, using a pulse wave analysis method in which a blood pressure is estimated on the basis of a waveform of a pulse wave. For example, the processor 230 may extract feature points of a measured pulse wave and estimate the blood pressure on the basis of characteristic values corresponding to the feature points and the blood pressure estimation formula. In this case, the blood pressure estimation formula may define the relationship between the characteristic value corresponding to each feature point of the pulse wave and the blood pressure. In this example, the processor 230 may extract feature points of the measured pulse wave, and update the blood pressure estimation formula on the basis of the estimated reference blood pressure value and the characteristic values corresponding to the extracted feature points.

The feature point may include a start point, the maximum point and the minimum point of the pulse wave or the ECG. The blood pressure estimation formula may be stored in an internal memory of the processor 230 or an external memory.

<Calibration Mode>

The processor 230 may operate in calibration mode according to a user's command or a set calibration interval.

In calibration mode, when the user pressurizes and depressurizes the blood pressure measurement apparatus 110 using the portable pressure measurement apparatus 120, the processor 230 may update the blood pressure formula using pressure data measured by the portable pressure measurement apparatus 120 during the process of pressurizing and depressurizing, that is, pressure data applied to the blood pressure measurement apparatus 110, and pulse wave data measured by the pulse wave measurer 210 during the process of pressurizing and depressurizing.

According to an example embodiment, the processor 230 may estimate a reference blood pressure value (e.g., MAP, SBP, DBP, etc.) using an oscillometric method on the basis of the pressure data measured by the portable pressure measurement device 120 and the pulse wave data measured by the pulse wave measurer 210 during the process of pressurizing and depressurizing, and update the blood pressure estimation formula on the basis of the estimated reference blood pressure value.

According to an example embodiment, when entering into calibration mode, the processor 230 may provide calibration guide information on a method of calibration using the portable pressure measurement apparatus 120 to the user. In this case, the calibration guide information may include information about a method of pressurizing and depressurizing the blood pressure measurement apparatus 110 using the portable pressure measurement apparatus 120.

Figure 3:
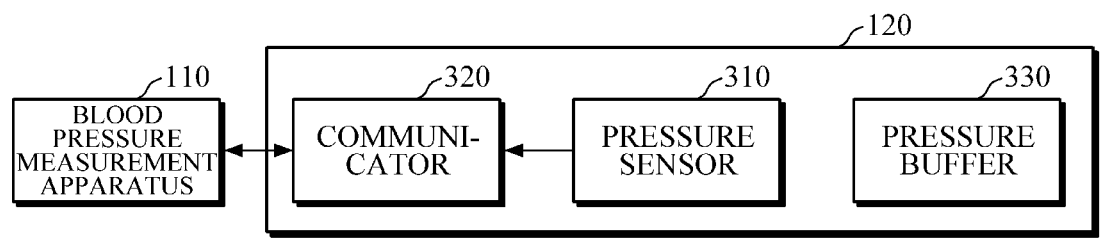
FIG. 3 is a block diagram illustrating a portable pressure measurement apparatus according to an example embodiment.

FIG. 3 is a block diagram illustrating a portable pressure measurement apparatus 120 according to an example embodiment.

Referring to FIG. 3, the portable pressure measurement apparatus 120 includes a pressure sensor 310 and a communicator 320.

The pressure sensor 310 may measure pressure data applied to a blood pressure measurement apparatus 110 while a user pressurizes and depressurizes the blood pressure measurement apparatus 110 using the portable pressure measurement apparatus 120.

The communicator 320 may transmit the measured pressure data to the blood pressure measurement apparatus 110. In this case, the communicator 320 may use various communication technologies, such as a Bluetooth communication, a BLE communication, an NFC, a WLAN communication, a ZigBee communication, an IrDA communication, a WFD communication, a UWB communication, an Ant+ communication, a Wi-Fi communication, a RFID communication, a 3G communication, a 4G communication, a 5G communication, and the like. However, these are examples, and the communication technologies are not limited to the above examples.

According to an example embodiment, the portable pressure measurement apparatus 120 further includes a pressure buffer 330.

The pressure buffer 330 may be disposed on a surface that is in contact with the blood pressure measurement apparatus 110 when a pressure is applied to the blood pressure measurement apparatus 110, so that the pressure buffer 330 may reduce the irregularity that may occur while the user pressurizes and depressurizes the blood pressure measurement apparatus 110 using the portable pressure measurement apparatus 120. In other words, the pressure buffer 330 may be used to maintain a linear pressure change in the process of pressurizing and depressurizing the blood pressure measurement apparatus 110, using the portable pressure measurement apparatus 120.

According to an example embodiment, the pressure buffer 330 may be implemented with a material, such as latex, polymer, sponge, and the like.

Figure 4:
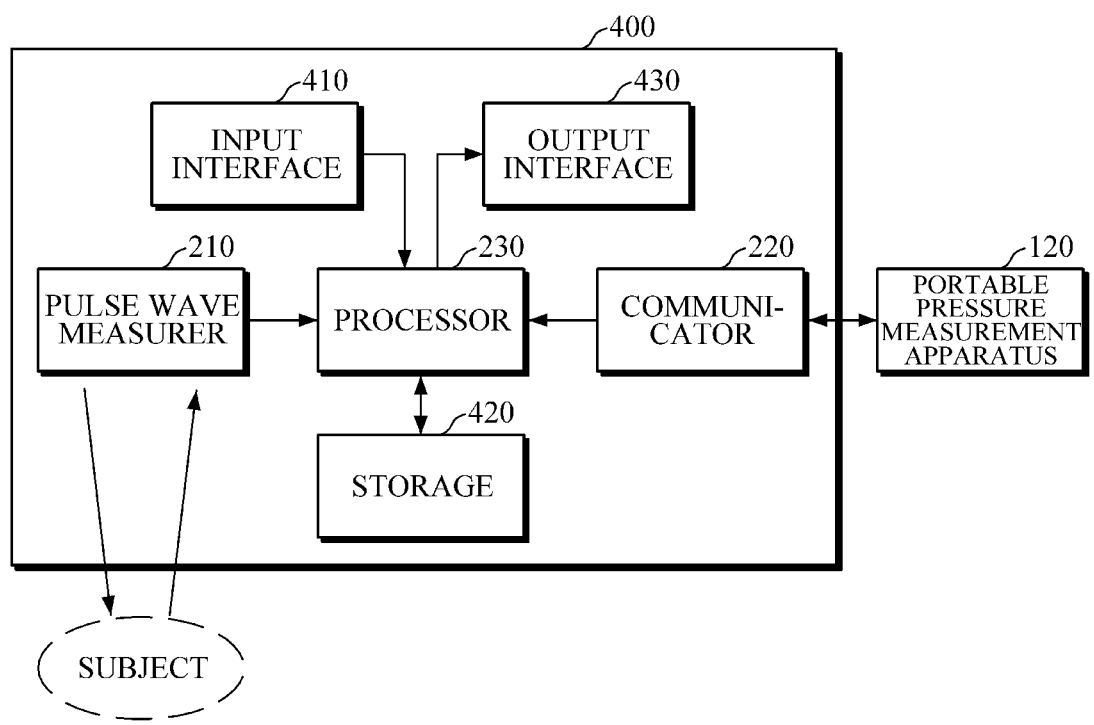
FIG. 4 is a diagram illustrating a blood pressure measurement apparatus according to another example embodiment.

FIG. 4 is a diagram illustrating a blood pressure measurement apparatus 400 according to another example embodiment.

Referring to FIG. 4, the blood pressure measurement apparatus 400 includes an input interface 410, a storage 420, an output interface 430, a pulse wave analyzer 210, a communicator 220, and a processor 230. In this case, because the pulse wave measurer 210, the communicator 220, and the processor 230 have been described with reference to FIG. 2, detailed descriptions thereof will be omitted.

The input interface 410 may receive various operation signals from the user. According to an example embodiment, the input interface 410 may include a key pad, a dome switch, a touch pad (resistive/capacitive) a jog wheel, a jog switch, a hardware button, and the like. When the touch pad forms a mutual layer structure with a display, it may be referred to as a touch screen.

The storage 420 may store a program or instructions for operations of the blood pressure measurement apparatus 400 and may store data input to or output from the blood pressure measurement apparatus 400. In addition, the storage 420 may store data related to the subject's pulse wave data measured by the pulse wave measurer 210, the blood pressure estimation formula used for blood pressure estimation, and the subject's blood pressure data estimated by the processor 230.

The storage 420 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like. In addition, the blood pressure measurement apparatus 400 may operate an external storage medium, such as a web storage, which performs the storage function of the storage 420 on the Internet.

The output interface 430 may output blood pressure estimation result, calibration guide information, and the like. According to an example embodiment, the output interface 430 may output the blood pressure estimation result, the calibration guide information, and the like in any one or any combination of audible, visual, and tactile manners. For example, the output interface 430 may output the blood pressure estimation result, the calibration guide information, and the like using a voice, text, vibration, etc. To this end, the output interface 430 may include a display, a speaker, a vibrator, etc.

Figure 5:
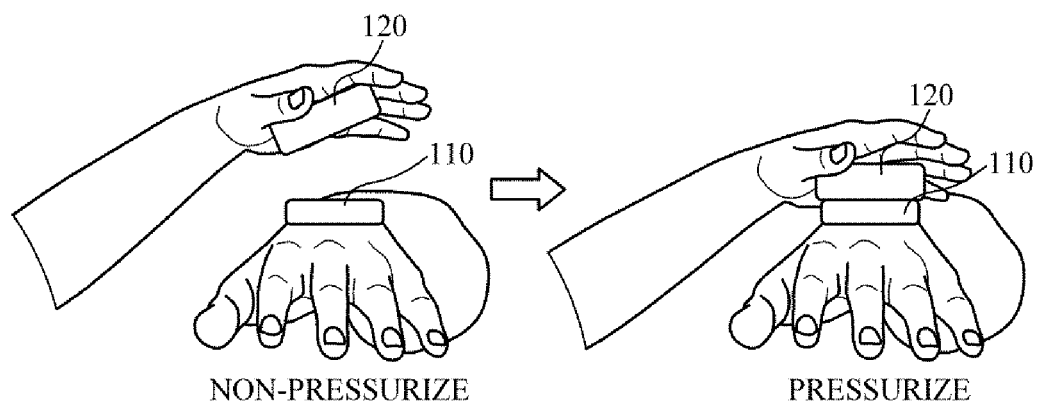
FIG. 5 is a diagram for describing a method of pressurizing a blood pressure measurement apparatus, according to an example embodiment.

FIG. 5 is a diagram for describing a method of pressurizing a blood pressure measurement apparatus, according to an example embodiment.

As shown in FIG. 5, the user may place a blood pressure measurement apparatus 110 on a subject, that is, the wrist of the user, and apply a pressure onto an upper part of the blood pressure measurement apparatus 110 with the other hand using a portable pressure measurement apparatus 120.

Figure 6:
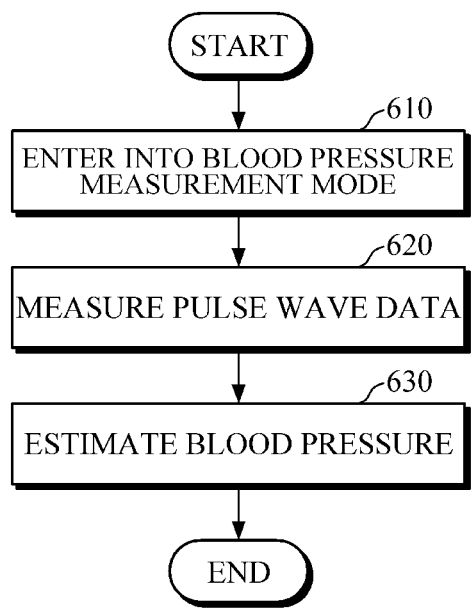
FIG. 6 is a flowchart illustrating a blood pressure measurement method according to an example embodiment.

FIG. 6 is a flowchart illustrating a blood pressure measurement method according to an example embodiment. The blood pressure measurement method of FIG. 6 may be an example embodiment of an operation method of the blood pressure measurement apparatus 110 in blood pressure measurement mode described above.

Referring to FIGS. 1 and 6, the blood pressure measurement apparatus 110 enters into blood pressure measurement mode according to a user's command, as depicted in operation 610.

The blood pressure measurement apparatus 110 measures pulse wave data of the subject, as depicted in operation 620. For example, the blood pressure measurement apparatus 110 may emit light to the subject, detect light reflected from or absorbed by the subject, and acquire the pulse wave data of the subject from the detected optical signal.

The blood pressure measurement apparatus 110 estimates a blood pressure of the subject by analyzing the measured pulse wave data, as depicted in operation 630.

For example, the blood pressure measurement apparatus 110 may measure the blood pressure using a PAT method for estimating the blood pressure on the basis of a pulse wave signal and an ECG signal, a PTT method for estimating the blood pressure on the basis of a PTT, and a PWA method for estimating the blood pressure on the basis of analysis of the waveform of a pulse wave.

Figure 7:
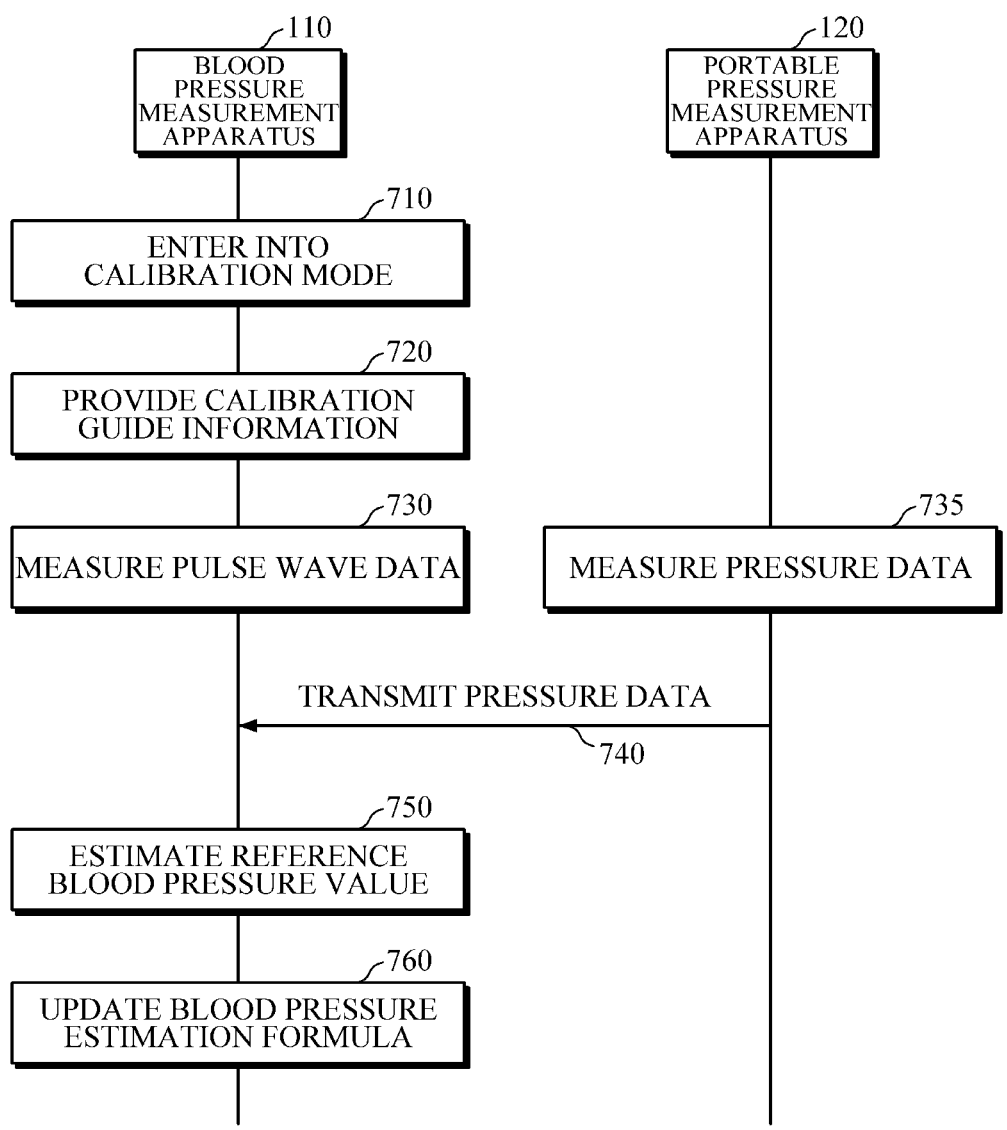
FIG. 7 is a flowchart illustrating a calibration method according to an example embodiment.

FIG. 7 is a flowchart illustrating a calibration method according to an example embodiment. The calibration method of FIG. 7 may be an example embodiment of an operation method of the cuffless blood pressure measurement system 100 in calibration mode described above.

Referring to FIGS. 1 and 7, the blood pressure measurement apparatus 110 enters into calibration mode according to a user's command or a set calibration interval, as depicted in operation 710.

When entering into calibration mode, the blood pressure measurement apparatus 110 provides calibration guide information on a method of calibrating the blood pressure measurement apparatus 110 using the portable pressure measurement apparatus 120, as depicted in operation 720.

When the user pressurizes and depressurizes the blood pressure measurement apparatus 110 using the portable pressure measurement apparatus 120 according to the calibration guide information, the blood pressure measurement apparatus 110 measures pulse wave data of the subject during the process of pressurizing and depressurizing, as depicted in operation 730.

The portable pressure measurement apparatus 120 measures pressure data applied to the blood pressure measurement apparatus 110 during the process of pressurizing and depressurizing, as depicted in operation 735, and transmits the measured pressure data to the blood pressure measurement apparatus 110, as depicted in operation 740.

The blood pressure measurement apparatus 110 estimates a reference blood pressure value on the basis of the measured pulse wave data and the received pressure data, as depicted in operation 750. For example, the blood pressure measurement apparatus 110 may estimate the reference blood pressure value by performing an oscillometric method on the basis of the measured pulse wave data and the received pressure data.

The blood pressure measurement apparatus 110 updates a blood pressure estimation formula on the basis of the estimated reference blood pressure value, as depicted in operation 760.

Figure 8:
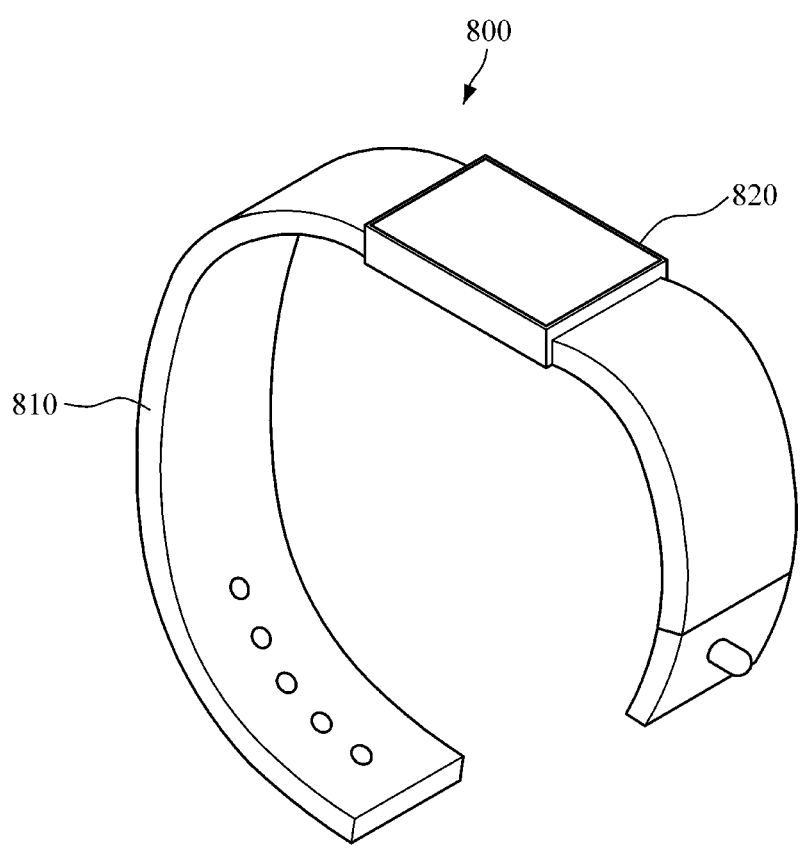
FIG. 8 is a diagram illustrating an implementation of a blood pressure measurement apparatus, according to an example embodiment.

FIG. 8 is a diagram illustrating an implementation of a blood pressure measurement apparatus, according to an example embodiment. As shown in FIG. 8, example embodiments of the blood pressure measurement apparatus described above may be implemented as a wrist wearable device.

Referring to FIG. 8, a wrist wearable device 800 includes a strap 810 and a main body 820.

The strap 810 may be formed to be flexible, and may be bent to wrap around or be separated from the user's wrist.

The main body 820 may include the respective components of the blood pressure measurement apparatus 110 or 400 illustrated in FIG. 2 or FIG. 4.

The pulse wave measurer 210 of FIG. 2 or 4 may be disposed on a lower part of the main body 820, that is, a surface that is in contact with the user's skin when the user wears the wrist wearable device 800.

Figure 9:
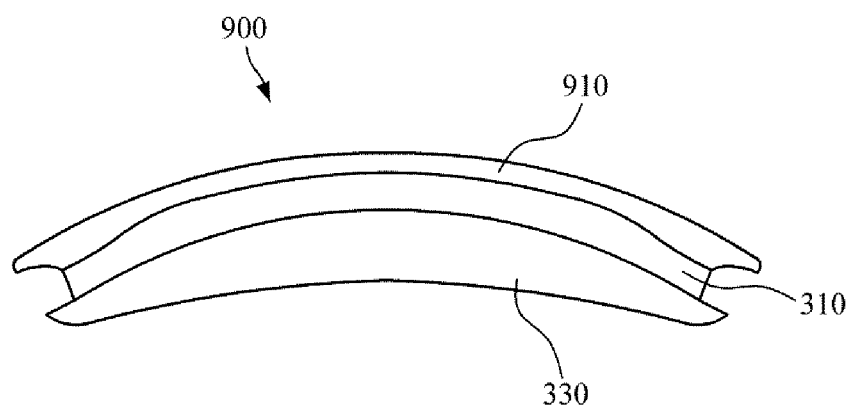
FIG. 9 is a diagram illustrating an implementation of a portable pressure measurement apparatus, according to an example embodiment.

FIG. 9 is a diagram illustrating an implementation of a portable pressure measurement apparatus 900, according to an example embodiment. As shown in FIG. 9, the upper surface of the portable pressure measurement apparatus 900 may be curved so that the user can easily pressurizes the portable pressure measurement apparatus 900 by placing the hand on the upper part.

Referring to FIG. 9, the portable pressure measurement apparatus 900 includes a main body 910, a pressure sensor 310, and a pressure buffer 330.

The main body 910 may include a communicator 320 therein.

The pressure sensor 310 may be disposed on the lower part of the main body 910. However, this is an example embodiment, and the position of the pressure sensor 310 may not be limited thereto. Thus, the pressure sensor 310 may be disposed at various positions, such as the upper part of the main body 910.

The pressure buffer 330 may be disposed on the lower part of the portable pressure measurement apparatus 900 to be used for reducing the irregularity that may occur during the process of pressurizing and depressurizing the blood pressure measurement apparatus 110 using the portable pressure measurement apparatus 900.

Figure 10:
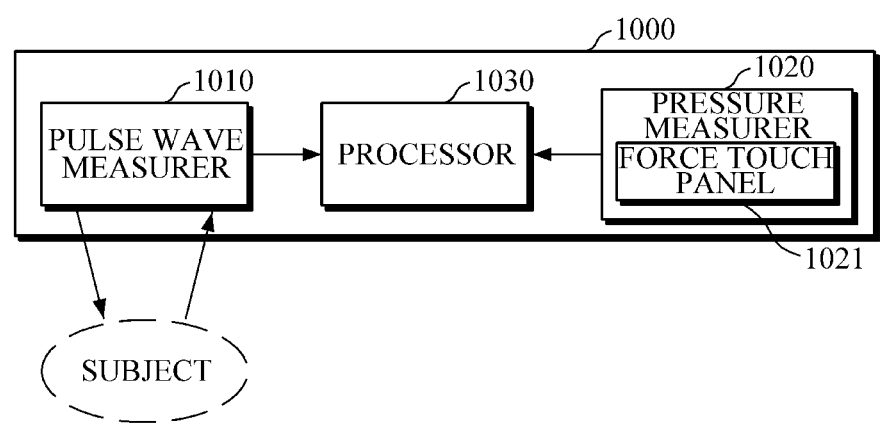
FIG. 10 is a block diagram illustrating a blood pressure measurement apparatus according to still another example embodiment.

FIG. 10 is a block diagram illustrating a blood pressure measurement apparatus 1000 according to still another example embodiment.

The blood pressure measurement apparatus 1000 may be a cuffless-type blood pressure measurement apparatus capable of non-invasively measuring a blood pressure of a subject. The blood pressure measurement apparatus 1000 may be implemented in the form of a software module or fabricated in the form of a hardware chip and mounted in an electronic device. In this case, the electronic device may include a mobile phone, a smartphone, a tablet computer, a notebook computer, a PDA, a PMP, a navigation system, an MP3 player, a digital camera, a wearable device, etc., and the wearable device may include a wristwatch type, a wrist band type, a ring type, a belt type, a necklace type, an ankle band type, a thigh band type, a forearm band type and the like. However, the electronic device is not limited to the above-described examples, and the wearable device is also not limited to the above-described example.

Referring to FIG. 10, the blood pressure measurement apparatus 1000 includes a pulse wave measurer 1010, a pressure measurer 1020, and a processor 1030.

The pulse wave measurer 1010 may measure pulse wave data of the subject. For example, the pulse wave measurer 1010 may emit light to the subject, detect light reflected from or absorbed by the subject, and acquire the pulse wave data of the subject from the detected optical signal.

The pressure measurer 1020 may measure pressure data that the user applies to the blood pressure measurement apparatus 1000. To this end, the pressure measurer 1020 may include a force touch panel 1021. For example, the pressure measurer 1020 may sense a touch area of the force touch panel 1021 that the user touches and the force that the user applies to the force touch panel 1021, and calculate the pressure applied to the blood pressure measurement apparatus 1000 on the basis of the sensed touch area and force.

The processor 1030 may operate in blood pressure measurement mode and in calibration mode.

The operations of the processor 1030 in blood pressure measurement mode are the same as those described with reference to FIG. 2, and hence detailed descriptions thereof will be omitted.

Hereinafter, operations of the processor 1030 in calibration mode will be described in detail.

<Calibration Mode>

The processor 1030 may operate in calibration mode according to a user's command or a set calibration interval.

In calibration mode, when the user pressurizes and depressurizes the force touch panel 1021, the processor 1030 may update a blood pressure estimation formula on the basis of pressure data measured by the pressure measurer 1020 and pulse wave data measured by the pulse wave measurer 1010 during the process of pressurizing and depressurizing.

According to an example embodiment, the processor 1030 may estimate a reference blood pressure value (e.g., MAP, SBP, DBP, etc.) using an oscillometric method on the basis of the pressure data measured by the pressure measurer 1020 and the pulse wave data measured by the pulse wave measurer 1010 during the process of pressurizing and depressurizing, and update the blood pressure estimation formula on the basis of the estimated reference blood pressure value.

According to an example embodiment, when entering into calibration mode, the processor 1030 may provide calibration guide information on a method of calibration using the force touch panel 1021 to the user. In this case, the calibration guide information may include information about a method of pressurizing and depressurizing the force touch panel 1021.

Figure 11:
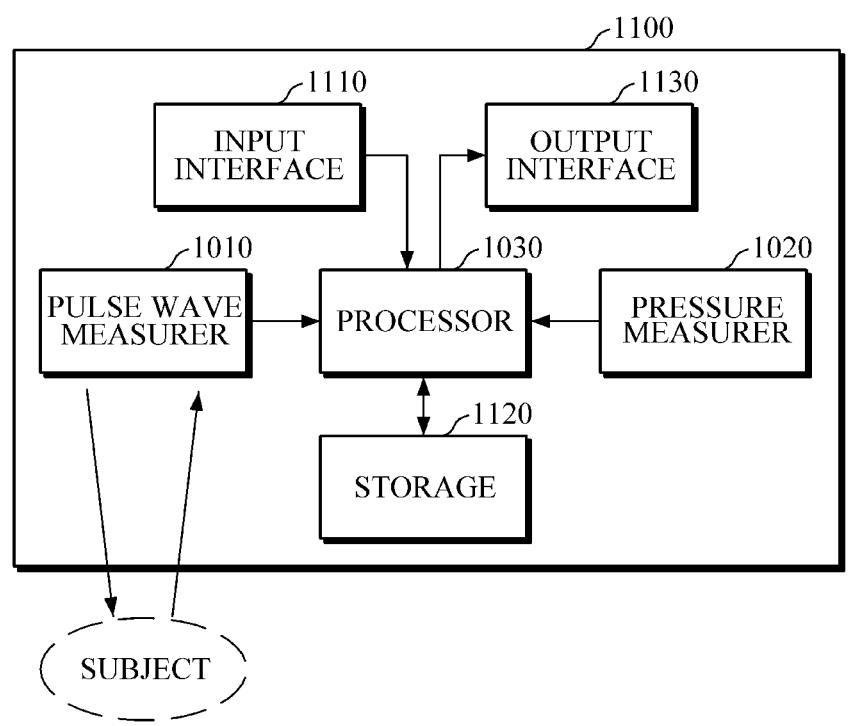
FIG. 11 is a diagram illustrating a blood pressure measurement apparatus according to yet another example embodiment.

FIG. 11 is a diagram illustrating a blood pressure measurement apparatus 1100 according to yet another example embodiment.

Referring to FIG. 11, the blood pressure measurement apparatus 1100 includes an input interface 1110, a storage 1120, an output interface 1130, a pulse wave measurer 1010, a pressure measurer 1020, and a processor 1030. In this case, the pulse wave measurer 1010, the pressure measurer 1020, and the processor 1030 have been described with reference to FIG. 10, and hence detailed descriptions thereof will be omitted.

The input interface 1110 may receive various operation signals from the user. According to an example embodiment, the input interface 1110 may include a key pad, a dome switch, a touch pad (resistive/capacitive) a jog wheel, a jog switch, a hardware button, and the like. When the touch pad forms a mutual layer structure with a display, it may be referred to as a touch screen.

The storage 1120 may store a program or instructions for operations of the blood pressure measurement apparatus 1100 and may store data input to or output from the blood pressure measurement apparatus 1100. In addition, the storage 1120 may store data related to the subject's pulse wave data measured by the pulse wave measurer 1110, the blood pressure estimation formula used for blood pressure estimation, and the subject's blood pressure data estimated by the processor 1030.

The storage 1120 may include a flash memory, a hard disk, a micro type multimedia card, and a card type memory (e.g., SD or XD memory), a RAM, an SRAM, a ROM, an EEPROM, a PROM, a magnetic memory, a magnetic disk, an optical disk, and the like. In addition, the blood pressure measurement apparatus 1100 may operate an external storage medium, such as a web storage, which performs the storage function of the storage 1120 on the Internet.

The output interface 1130 may output blood pressure estimation result, calibration guide information, and the like. According to an example embodiment, the output interface 1130 may output the blood pressure estimation result, the calibration guide information, and the like in any one or any combination of audible, visual, and tactile manners. For example, the output interface 1130 may output the blood pressure estimation result, the calibration guide information, and the like using a voice, text, vibration, etc. To this end, the output interface 1130 may include a display, a speaker, a vibrator, etc.

Figure 12:
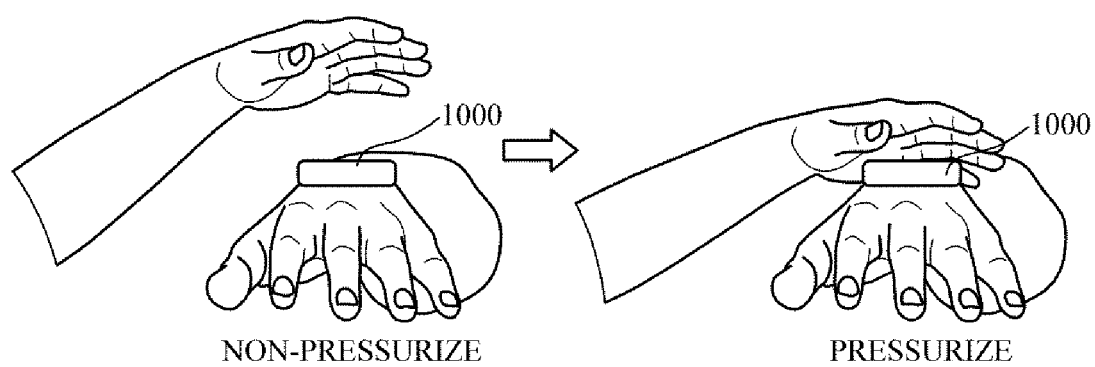
FIG. 12 is a diagram for describing a method of pressurizing a blood pressure measurement apparatus, according to an example embodiment.

FIG. 12 is a diagram for describing a method of pressurizing a blood pressure measurement apparatus 1000, according to an example embodiment.

As shown in FIG. 12, the user may place the blood pressure measurement apparatus 1000 on a subject, that is, the wrist of the user, and apply a pressure onto a force touch panel disposed on the upper part of the blood pressure measurement apparatus 1000 with the other hand.

Figure 13:
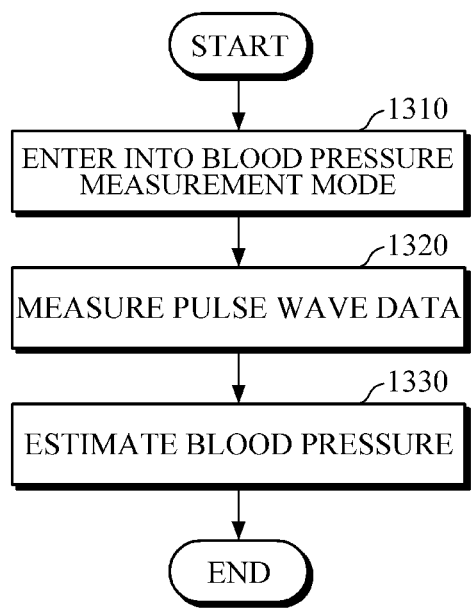
FIG. 13 is a flowchart illustrating a blood pressure measurement method according to another example embodiment.

FIG. 13 is a flowchart illustrating a blood pressure measurement method according to an example embodiment. The blood pressure measurement method of FIG. 13 may be an example embodiment of the operation method of the above-described blood pressure measurement apparatus 1000 in blood pressure measurement mode.

Referring to FIGS. 10 and 13, the blood pressure measurement apparatus 1000 enters into blood pressure measurement mode according to a user's command, as depicted in operation 1310.

The blood pressure measurement apparatus 1000 measures pulse wave data of a subject, as depicted in operation 1320.

The blood pressure measurement apparatus 1000 estimates a blood pressure of the subject by analyzing the measured pulse wave data, as depicted in operation 1330.

Figure 14:
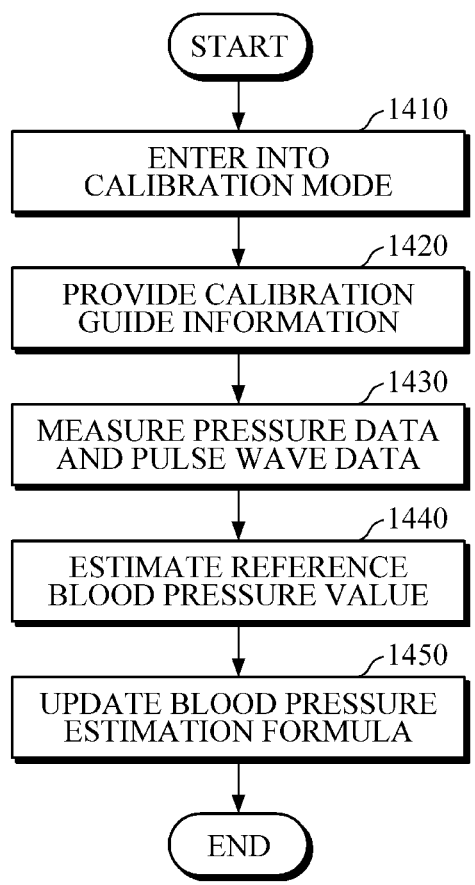
FIG. 14 is a flowchart illustrating a calibration method according to another example embodiment.

FIG. 14 is a flowchart illustrating a calibration method according to an example embodiment. The calibration method of FIG. 14 may be an example embodiment of the operation method of the above-described blood pressure measurement apparatus 1000 in calibration mode.

Referring to FIGS. 10 and 14, the blood pressure measurement apparatus 1000 enters into calibration mode according to a user's command or a set calibration interval, as depicted in operation 1410.

When entering into calibration mode, the blood pressure measurement apparatus 1000 provides calibration guide information on a method of calibrating the blood pressure measurement apparatus 1000 using the force touch panel 1021, as depicted in operation 1420.

When the user pressurizes and depressurizes the force touch panel 1021 according to the calibration guide information, the blood pressure measurement apparatus 1000 measures pulse wave data of the subject and pressure data applied to the force touch panel 1021 during the process of pressurizing and depressurizing, as depicted in operation 1430.

The blood pressure measurement apparatus 1000 estimates a reference blood pressure value on the basis of the measured pulse wave data and pressure data, as depicted in operation 1440. For example, the blood pressure measurement apparatus 1000 may estimate the reference blood pressure value by performing an oscillometric method on the basis of the measured pulse wave data and the measured pressure data.

The blood pressure measurement apparatus 1000 updates a blood pressure estimation formula on the basis of the estimated reference blood pressure value, as depicted in operation 1450.

The current example embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A blood pressure measurement apparatus comprising:
a pulse wave measurer configured to measure pulse wave data of a subject while a user manually pressurizes the blood pressure measurement apparatus with an external portable pressure measurement apparatus that is externally engaged to the blood pressure measurement apparatus on an upper surface of the blood pressure measurement apparatus, wherein a lower surface of the blood pressure measurement apparatus is opposite to the upper surface of the blood pressure measurement apparatus and faces a skin of the subject;
a communicator configured to receive, from the external portable pressure measurement apparatus, pressure data that is applied to the blood pressure measurement apparatus by the external portable pressure measurement apparatus during the pressurizing of the blood pressure measurement apparatus, the pressure data being measured by the external portable pressure measurement apparatus; and
a processor configured to update a blood pressure estimation formula, based on the received pressure data and the measured pulse wave data.

2. The blood pressure measurement apparatus of claim 1, wherein the pulse wave measurer is further configured to:
emit light to the subject;
detect light that is reflected from or absorbed by the subject to which the light is emitted; and
acquire the pulse wave data of the subject, based on the detected light.

3. The blood pressure measurement apparatus of claim 1, wherein the processor is further configured to:
estimate a reference blood pressure value by performing an oscillometric method, based on the received pressure data and the measured pulse wave data; and
update the blood pressure estimation formula, based on the estimated reference blood pressure value.

4. The blood pressure measurement apparatus of claim 1, wherein the processor is further configured to provide calibration guide information of a method of calibration using the external portable pressure measurement apparatus by placing the external portable pressure measurement apparatus external to the blood pressure measurement apparatus on the upper surface of the blood pressure measurement apparatus.

5. The blood pressure measurement apparatus of claim 4, wherein the calibration guide information comprises information of a method of the pressurizing of the blood pressure measurement apparatus by placing the external portable pressure measurement apparatus external to the blood pressure measurement apparatus on the upper surface of the blood pressure measurement apparatus.

6. The blood pressure measurement apparatus of claim 1, wherein the blood pressure measurement apparatus is a wrist wearable device.

7. A calibration method for a blood pressure measurement apparatus, the calibration method comprising:
measuring pulse wave data of a subject while a user manually pressurizes the blood pressure measurement apparatus with an external portable pressure measurement apparatus that is externally engaged to the blood pressure measurement apparatus on an upper surface of the blood pressure measurement apparatus, wherein a lower surface of the blood pressure measurement apparatus is opposite to the upper surface of the blood pressure measurement apparatus and faces a skin of the subject;

receiving, from the external portable pressure measurement apparatus, pressure data that is applied to the blood pressure measurement apparatus by the external portable pressure measurement apparatus during the pressurizing of the blood pressure measurement apparatus, the pressure data being measured by the external portable pressure measurement apparatus; and updating a blood pressure estimation formula, based on the received pressure data and the measured pulse wave data.

8. The calibration method of claim 7, wherein the updating of the blood pressure estimation formula comprises:

estimating a reference blood pressure value by performing an oscillometric method, based on the received pressure data and the measured pulse wave data; and updating the blood pressure estimation formula, based on the estimated reference blood pressure value.

9. The calibration method of claim 7, further comprising providing calibration guide information of a method of calibration using the external portable pressure measurement apparatus by placing the external portable pressure measurement apparatus external to the blood pressure measurement apparatus on the upper surface of the blood pressure measurement apparatus.

10. The calibration method of claim 9, wherein the calibration guide information comprises information of a method of the pressurizing of the blood pressure measurement apparatus by placing the external portable pressure measurement apparatus external to the blood pressure measurement apparatus on the upper surface of the blood pressure measurement apparatus.

* * * * *